United States Patent
Whitney et al.

(10) Patent No.: US 6,180,660 B1
(45) Date of Patent: *Jan. 30, 2001

(54) CHOLESTEROL-LOWERING THERAPY

(75) Inventors: Edwin J. Whitney, San Antonio, TX (US); Geraldine Mantell, North Wales, PA (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/078,087

(22) Filed: May 13, 1998

Related U.S. Application Data

(60) Provisional application No. 60/056,966, filed on Aug. 26, 1997, and provisional application No. 60/076,859, filed on Mar. 5, 1998.

(51) Int. Cl.$^7$ ................................................ A61K 31/35
(52) U.S. Cl. .......................... 514/451; 514/460; 514/824
(58) Field of Search .................................. 514/451, 460, 514/824

(56) References Cited

U.S. PATENT DOCUMENTS

| | | | |
|---|---|---|---|
| H1286 | 2/1994 | Eisman et al. | 514/91 |
| 5,140,012 | 8/1992 | McGovern et al. | 514/19 |
| 5,622,985 | 4/1997 | Olukotun et al. | 514/423 |
| 5,674,893 | 10/1997 | Behounek | 514/451 |
| 5,691,375 | * 11/1997 | Behounek et al. | 514/510 |
| 5,807,834 | * 9/1998 | Morehouse | 514/26 |

FOREIGN PATENT DOCUMENTS

| | | | |
|---|---|---|---|
| 0 461 548 | * | 12/1991 | (EP) . |
| 461 548 | * | 12/1991 | (EP) . |
| 0 528 515 | * | 2/1993 | (EP) . |
| 0 671 171 | * | 9/1995 | (EP) . |
| 671 170 | * | 9/1995 | (EP) . |
| 738 512 | | 10/1996 | (EP) . |

OTHER PUBLICATIONS

Cholesterol Treatment Trialists'(CTT) Collaboration, "Protocol for Prospective Collaborative . . . ", American Journal of Cardiology, vol. 75, pp. 1130–1134, Jun. 1, 1995.

J. R. Downs et al., "Design & Rationale of the Air Force . . . ", American Journal of Cardiology, vol. 80, pp. 287–293, Aug. 1, 1997.

PR Newswire, p. 1112NYW031, Mevacor(R) Reduces First Heart Attacks, Other Coronary Events by 36 Percent in Landmark Study of Healthy People, Nov. 12, 1997.

"Merck Mevacor AFCAPS/TEXCAPS results could expand patient population", FDC Reports Prescription Pharmaceuticals and Biotechnology, vol. 59, No. 46, p. T&G–6, Nov. 17, 1997.

Marketletter Publications Ltd. (UK), "Mevacor Study May Extend Lipid–Lowering Therapy", Nov. 17, 1997.

PR Newswire, p. 1124DAM006, "UNT Health Science Center Produces Results in Major Cholesterol Study", Nov. 24, 1997.

Genesis Group Associates, Inc., "And Also of Note . . . ", Genesis Report–Rx, vol. 7, No. 1, Dec. 1, 1997.

"Progress in Clinical Trials", Clininical Cardiology, vol. 21, p. 52, Jan. 1998.

Marketletter Publications Ltd. (UK), "Final AFCAPS Data Confirm Benefits of Lowering Average Lipids", Apr. 27, 1998.

J. R. Downs et al., "Primary Prevention of Acute Coronary . . . ", Journal of the American Medical Association, vol. 279, No. 20, pp. 1615–1622, May 27, 1998.

R. S. Rosenson et al., "Antiatherothrombotic Properties of Statins", Journal of the American Medical Association, vol. 279, No. 20, pp. 1643–1650, May 27, 1998.

Thomas A. Pearson, "Lipid–lowering Therapy in Low–Risk Patients", Journal of the American Medical Association, vol. 279, No. 20, pp. 1659–1661, May 27, 1998.

Probstfield, J. L. et al., "Results of the primary outcome measure . . . ", American Journal of Cardiology, vol. 76, No. 9, pp. 47C–53C, (1995).

Marcus, A., "Role of HMG–CoA reductase inhibtors in the treatment . . . ", Cardiovascular Reviews and Reports, pp. 10–11, 15–16, 21–24, and 26–27, Jan. 1996.

Meiser, B. M., et al., "Simvastatin decreases accelerated graft vessel disease (GFD) . . . ", Transplant. Proc., vol. 25, (2), pp. 2077–9, Apr. 1993.

Kellick, K. A., et al., "Outcome monitoring of fluvastatin in a Department of Veterans . . . ", American Journal of Cardiology, vol. 76 (2), pp. 62A–64A, Jul. 13, 1995.

Motomura, N., et al., "HMG–CoA Reductase Inhibitors in Organ Transplantation", Journal of Nephrology, vol. 10 (2), pp. 68–76, (1997).

Haria, M., et al., "Pravastatin—A Reappraisal of its Pharmacological Properties . . . ", Drugs, vol. 53 (2), pp. 299–336, Feb. 1997.

Stein, E., et al., "Cerivastatin, a New Potent Synthetic HMG Co–A Reductase Inhibitor . . . ", Journal of Cardiovascular Pharmacology and Theraputics, vol. 2 (1), pp. 7–16, (1997).

Pfeifer, M.A., et al., "Cholesterol and Recurrent Events: A Secondary . . . ", American Journal of Cardiology, vol. 76 (9), pp. 98C–106C, Sep. 28, 1995.

(List continued on next page.)

*Primary Examiner*—Kimberly Jordan
(74) *Attorney, Agent, or Firm*—Carol S. Quagliato; Melvin Winokur

(57) ABSTRACT

Methods are described for preventing or reducing the risk of a first occurrence of a cardiovascular event using an HMG-CoA reductase inhibitor alone or in combination with another lipid altering agent. Subjects to be treated are those having an average serum total cholesterol level, an average to mildly elevated serum low-density lipoprotein cholesterol level, and a below average serum high-density lipoprotein cholesterol level, with no history of clinically evident coronary disease.

38 Claims, No Drawings

OTHER PUBLICATIONS

Husten, L., "Latest Trials on Statins show large benefits for wide range of patients," Lancet, vol. 350, Issue 9090, p. 1525, Nov. 22, 1997.

Pharmaceutical Approvals Monthly, Clinical Trial Briefs: Merck, vol. 2, Issue 12, Dec. 1, 1997.

Drug News & Perspectives, R&D Briefs, "New Data Show Economic Benefits of Cholesterol Lowering in Healthy Population", Apr. 28, 1998.

Southworth, M. R., et al., "The Use of HMG–Co–A Reductase Inhibitors to Prevent Accelerated Graft . . . ", Annals of Pharmacotherapy, vol. 31 (4), pp. 489–91, (1997).

* cited by examiner

US 6,180,660 B1

CHOLESTEROL-LOWERING THERAPY

This application claims benefit of U.S. Provisional Application Nos. 60/056,966, filed Aug. 26, 1997, and 60/076,859, filed Mar. 5, 1998.

FIELD OF THE INVENTION

The instant invention involves a method of using a cholesterol reducing agent such as a 3-hydroxy-3-methylglutaryl coenzyme A (HMG-CoA) reductase inhibitor (or HMG-CoA RI) alone or in combination with other lipid altering agents for preventing or reducing the risk of first occurrence of a cardiovascular event.

BACKGROUND OF THE INVENTION

It has been clear for several decades that elevated blood cholesterol is a major risk factor for coronary heart disease (CHD), and many studies have shown that the risk of CHD events can be reduced by lipid-lowering therapy. Prior to 1987, the lipid-lowering armamentarium was limited essentially to a low saturated fat and cholesterol diet, the bile acid sequestrants (cholestyramine and colestipol), nicotinic acid (niacin), the fibrates and probucol. Unfortunately, all of these treatments have limited efficacy or tolerability, or both. With the introduction of lovastatin, the first inhibitor of HMG-CoA reductase to become available for prescription in 1987, for the first time physicians were able to obtain comparatively large reductions in plasma cholesterol with very few adverse effects.

Recent studies have unequivocally demonstrated that lovastatin, simvastatin, and pravastatin, which are members of the HMG-CoA reductase inhibitor class, slow the progression of atherosclerotic lesions in the coronary and carotid arteries. Simvastatin and pravastatin have also been shown to reduce the risk of coronary heart disease events in patients with hypercholesterolemia and/or CHD, and in the case of simvastatin a highly significant reduction in the risk of coronary death and total mortality has been shown by the Scandinavian Simvastatin Survival Study. This study also provided evidence for a reduction in cerebrovascular events. Additional studies have shown that HMG CoA RI's may have an effect on platelet aggregation.

SUMMARY OF THE INVENTION

One object of the instant invention is to provide a novel method for preventing or reducing the risk of a first occurrence of a cardiovascular event in a subject having an average to mildly elevated level of LDL cholesterol, and below average high-density lipoprotein (HDL) cholesterol, with no clinical evidence of coronary heart disease, comprising administering a prophylactically effective amount of a lipid altering agent such as an HMG-CoA reductase inhibitor either alone or in combination with another lipid altering agent such as a fibrate, or niacin to the subject. Additional objects will be evident from the following detailed description.

DETAILED DESCRIPTION OF THE INVENTION

Examples of HMG-CoA reductase inhibitors that may be used include but are not limited to lovastatin (MEVACOR®; see U.S. Pat. No. 4,231,938), simvastatin (ZOCOR®; see U.S. Pat. No. 4,444,784), pravastatin (PRAVACHOL®; see U.S. Pat. No. 4,346,227), fluvastatin (LESCOL®; see U.S. Pat. No. 5,354,772), atorvastatin (LIPITOR®; see U.S. Pat. No. 5,273,995) and cerivastatin (also known as rivastatin; see U.S. Pat. No. 5,177,080), and the pharmaceutically acceptable salt, ester and lactone forms thereof. The structural formulas of these and additional HMG-CoA reductase inhibitors that may be used in the instant methods are described at page 87 of M. Yalpani, "Cholesterol Lowering Drugs", Chemistry & Industry, pp. 85–89 (Feb. 5, 1996). The HMG-CoA RI is selected from lovastatin, cerivastatin, atorvastatin, pravastatin and simvastatin, a sub-class comprises simvastatin and lovastatin. Examples of fibrates that may be used in combination with the HMG-CoA RI include, but are not limited to benzofibrate, ciprofibrate, fenofibrate, gemfibrazol and clofibrate.

The term HMG-CoA reductase inhibitor is intended to include all pharmaceutically acceptable salt, ester and lactone forms of compounds which have HMG-CoA reductase inhibitory activity, and therefore the use of such salts, esters and lactone forms is included within the scope of this invention.

Compounds which have inhibitory activity for HMG-CoA reductase can be readily identified by using assays well-known in the art. For example, see the assays described or cited in U.S. Pat. Nos. 4,231,938 at col. 6, and WO 84/02131 at pp. 30–33.

Ester derivatives of the described compounds may act as prodrugs which, when absorbed into the bloodstream of a warm-blooded animal, may cleave in such a manner as to release the drug form and permit the drug to afford improved therapeutic efficacy.

Herein, the term "pharmaceutically acceptable salts" shall mean non-toxic salts of the compounds employed in this invention which are generally prepared by reacting the free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, valerate.

Prophylactically effective amounts of the HMG-CoA reductase inhibitors are suitable for use in the compositions and methods of the present invention. The term "prophylactically effective amount" is intended to mean that amount of a pharmaceutical drug that will prevent or reduce the risk of occurrence of the biological or medical event that is sought to be prevented of a tissue, a system, animal or human that is being sought by a researcher, veterinarian, medical doctor or other clinician. The dosage regimen utilizing an HMG-CoA RI is selected in accordance with a variety of factors including type, species, age, weight, sex and medical condition of the subject; the severity of the condition to be treated; the route of administration; the renal and hepatic function of the subject; and the particular compound or salt or ester thereof employed. A consideration of these factors is well within the purview of the ordinarily skilled clinician for the purpose of determining the prophylactically effective amounts of the drug needed to prevent or reduce the risk of occurrence of the condition sought to be prevented. In one embodiment, the prophylactically effective amount to be used in the methods of this invention is that amount of drug sufficient to lower the human subject's LDL cholesterol to a target level of 130 mg/dl or less; in a sub-embodiment to a target level of 115 mg/dl or less; and in a further sub-embodiment to a target level of 110 mg/dl or less. The ordinarily skilled clinician will be able to titrate the subject to the appropriate amount of lipid altering agent such as an HMG-CoA RI which, when taken on a daily basis, will allow the patient to reach this goal.

The term "patient" or "subject" includes mammals, especially humans, who take a lipid altering agent for any of the uses described herein. Administration of the lipid altering agent to the subject includes both self-administration and administration to the subject by another person.

Dosage information for HMG-CoA RI's is well known in the art, since several are marketed in the U.S. In particular, the daily dosage amounts of the HMG-CoA reductase inhibitor may be the same or similar to those amounts which are employed for anti-hypercholesterolemic treatment and which are described in the *Physicians' Desk Reference* (PDR). For example, see the 50$^{th}$ Ed. of the PDR, 1996 (Medical Economics Co); in particular, see at page 216 the heading "Hypolipidemics," sub-heading "HMG-CoA Reductase Inhibitors," and the reference pages cited therein. Preferably, the oral dosage amount of HMG-CoA RI is from about 1 to 200 mg/day, and more preferably from about 5 to 160 mg/day. However, dosage amounts will vary depending on the potency of the specific HMG-CoA reductase inhibitor used as well as other factors as noted above. An HMG-CoA RI which has sufficiently greater potency may be given in sub-milligram daily dosages.

As examples, the daily dosage amount for simvastatin may be selected from 5 mg, 10 mg, 20 mg, 40 mg, and 80 mg; for lovastatin, 10 mg, 20 mg, 40 mg and 80 mg; for fluvastatin sodium, 20 mg, 40 mg and 80 mg; and for pravastatin sodium, 10 mg, 20 mg, and 40 mg. The daily dosage amount for cerivastatin may be in the range of from 0.1 mg to 0.8 mg, and more particularly from 0.2 mg to 0.8 mg, including dosage amounts of 0.2 mg, 0.3 mg, 0.4 mg and 0.8 mg. Oral administration may be in single or divided doses of two, three, or four times daily, although a single daily dose of the HMG-CoA RI is preferred.

Pharmaceutical formulations for HMG-CoA reductase inhibitors are well-known to those skilled in the art, as evidenced by the information provided in the 1996 PDR. While the HMG-CoA reductase inhibitor can be administered orally or parenterally, oral dosing is preferred.

For example, the active agents employed in the instant therapy can be administered in such oral forms as tablets, capsules (each of which includes sustained release or timed release formulations), pills, powders, granules, elixirs, tinctures, suspensions, syrups, and emulsions. Oral formulations are preferred. The instant invention includes the use of oral rapid-release as well as time-controlled release pharmaceutical formulations, particularly as described in U.S. Pat. No. 5,366,738.

The active drug can be administered in admixture with pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices. See, for example, *Remington's Pharmaceutical Sciences*, Mack Publishing Co., Easton, Pa.

For instance, for oral administration in the form of a tablet or capsule, the active drug component can be combined with a non-toxic, pharmaceutically acceptable, inert carrier such as lactose, starch, sucrose, glucose, modified sugars, modified starches, methyl cellulose and its derivatives, dicalcium phosphate, calcium sulfate, mannitol, sorbitol and other reducing and non-reducing sugars, magnesium stearate, steric acid, sodium stearyl fumarate, glyceryl behenate, calcium stearate and the like. For oral administration in liquid form, the drug components can be combined with non-toxic, pharmaceutically acceptable inert carrier such as ethanol, glycerol, water and the like. Moreover, when desired or necessary, suitable binders, lubricants, disintegrating agents and coloring and flavoring agents can also be incorporated into the mixture. Stabilizing agents such as antioxidants (BHA, BHT, propyl gallate, sodium ascorbate, citric acid) can also be added to stabilize the dosage forms. Other suitable components include gelatin, sweeteners, natural and synthetic gums such as acacia, tragacanth or alginates, carboxymethylcellulose, polyethylene glycol, waxes and the like.

The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and cross linked or amphipathic block copolymers of hydrogels.

The methods of the invention may be used to prevent or reduce the risk of a first occurrence of a fatal or non-fatal cardiovascular event. The term "cardiovascular event" includes but is not limited to fatal and non-fatal acute major coronary events, coronary revascularization procedures, peripheral vascular disease, stable angina, and cerebrovascular insufficiency such as stroke.

The term "acute major coronary event" is intended to include fatal myocardial infarction; witnessed and unwitnessed sudden cardiac death and sudden death occurring from 1 hour up to 24 hours after collapse; non-fatal myocardial infarction including definite acute Q-wave myocardial infarction, non-Q-wave myocardial infarction, and silent subclinical (remote) myocardial infarction; and unstable angina pectoris. As used herein, the term "myocardial infarction" is intended to include both Q-wave and non-Q-wave myocardial infarction and silent subclinical (remote) myocardial infarction.

Subjects to be treated with the instant methods are those having an average to mildly elevated serum total cholesterol level, which is intended herein to be a level less than or equal to about 260 mg/dl. In particular, the patients to be treated may have a serum total cholesterol level of less than or equal to 240 mg/dl, and more particularly under 200 mg/dl. For example, the subjects to be treated may have a serum total cholesterol level from 180 mg/dl to 264 mg/dl. In one embodiment, the subjects to be treated have a below average high-density lipoprotein cholesterol level, i.e., less than or equal to 50 mg/dl, and an average to mildly elevated low-density lipoprotein cholesterol level, i.e., less than or equal to 190 mg/dl, prior to treatment. In another embodiment the low-density lipoprotein cholesterol level is 130 mg/dl to 190 mg/dl prior to treatment. In a still further embodiment, the LDL-cholesterol is <130 mg/dl if the ratio of total cholesterol to HDL-cholesterol is >6. The subjects to be treated also have no clinically evident coronary heart disease.

In accordance with this invention, a prophylactically effective amount of an HMG-CoA RI or a combination with another lipid altering agent can be used for the preparation of a medicament useful for preventing or reducing the risk of a first occurrence of a cardiovascular event in a subject having an average to mildly elevated level of serum total cholesterol, an average to mildly elevated level of low-density lipoprotein cholesterol, and a below average level of high-density lipoprotein cholesterol.

The following is a description of a clinical trial referred to herein as "AFCAPS/TexCAPS" or "AFCAPS" employing lovastatin to exemplify the methods of the present invention.

EXAMPLE 1

AFCAPS/TexCAPS was a primary prevention endpoint event trial which: (1) included unstable angina as a primary endpoint, reflecting the trend to treat coronary heart disease aggressively before a myocardial infarction has occurred; 2) involved aggressive pharmacologic intervention, with titration, to target an LDL-cholesterol goal lower than current National Cholesterol Education Panel guidelines for primary prevention; and 3) included a cohort comprised of men and women with a broad age range encompassing the elderly and included persons with a lipid profile consisting of average total and LDL-cholesterol, below average HDL-cholesterol levels; total cholesterol/HDL-cholesterol ratio greater than or equal to 4.5, with a baseline mean ratio of 6.1 for the cohort; and LDL/HDL-cholesterol ratio greater than or equal to 4.

Entrance inclusion criteria were LDL-cholesterol 130–190 mg/dl (or <130 if the ratio of total cholesterol/HDL is >6) and HDL-cholesterol $\leq$45 mg/dl for men and $\leq$47 mg/dl for women.

The trial was designed to study the effect of LDL-cholesterol reduction in a cohort with average to mildly elevated LDL-cholesterol and a below average HDL-cholesterol. National Cholesterol Education Panel guidelines for adults (see National Cholesterol Education Program Expert Panel, Summary of the second report of the National Cholesterol Education Program (NCEP) Expert Panel on Detection, Evaluation and Treatment of High Blood Cholesterol in Adults (Adult Treatment Panel II), *JAMA*, 1993;269:3015–3023) already incorporate HDL-cholesterol concentration in recommendations for estimating CHD risk and selecting lipid-altering therapy.

STUDY DESIGN

AFCAPS/TexCAPS was a double-blind, randomized, placebo controlled trial designed and powered to investigate whether chronic lipid-lowering, with lovastatin will decrease the rate of first acute major coronary events (e.g. sudden cardiac death, fatal and non-fatal myocardial infarction and unstable angina) compared to intervention with diet alone during at least 4.5 years of follow-up in a cohort without clinical evidence of atherosclerotic cardiovascular disease and with average to mildly elevated total cholesterol, average to midly elevated LDL-cholesterol, and below average HDL-cholesterol. Secondary objectives included whether chronic treatment with lovastatin, compared to placebo, would decrease cardiovascular morbidity and mortality across the spectrum of clinical events, by measuring the rates of: (1) fatal and non-fatal coronary revascularization procedures (2) unstable angina, (3) fatal and non-fatal myocardial infarction, (4) fatal and non-fatal cardiovascular events, (5) fatal and non-fatal coronary events.

All participants underwent dietitian taught group instruction in the American Heart Association Step 1 diet commencing at least 12 weeks prior to randomization (Week -12) and reinforced at Weeks -4 and -2. Baseline observations included collection of medical history, health habit and demographic data, physical exam, eye exam (San Antonio clinic only), chest X-ray, mammogram (women), electrocardiogram and analysis of lipids/lipoproteins, hematology, blood chemistry and urine. A 2-week placebo baseline run-in was followed by randomization of eligible compliant participants to treatment with lovastatin or placebo.

Participants included 6605 men and women with normal to mildly elevated total and LDL-cholesterol and below average HDL-cholesterol defined as: total cholesterol 180–264 mg/dl, LDL-cholesterol 130–190 mg/dl, HDL-cholesterol $\leq$45 mg/dl for men and $\leq$47 mg/dl for women and triglycerides $\leq$400 mg/dl. All lipid/lipoprotein entrance criteria had to be met on average at both four and two weeks prior to randomization (after at least eight weeks of diet therapy). In addition, for both total and LDL-cholesterol, the two eligibility determinations had to be within 15% of each other.

Excluded for clinical evidence of atherosclerotic cardiovascular disease were men and women who had: prior history of myocardial infarction; angina; claudication; cerebrovascular accident; or transient ischemic attack. Also excluded were those aged >73 years or <45 years (men) or <55 years (women) or those with secondary hyperlipoproteinemia, nephrotic syndrome, uncontrolled or insulin-dependent diabetes mellitus or uncontrolled hypertension. At their discretion, investigators also could have excluded those who would have difficulty completing a study of at least 5 years duration (e.g. due to compliance problems or reduced life expectancy).

Baseline risk factors in the tested population were as follows:
Family history of premature coronary artery disease: 16%;
Active cigarette smoker: 12%;
Hypertension: 22%;
Diabetes: 2%.
HDL <35 mg/dL: 35%

Participants were randomized to either placebo or lovastatin 20 mg once a day and were stratified by center and gender so that there was an equal chance of being assigned to lovastatin or placebo. Formal procedures ensured maintenance of the study blind. Participants, investigators, Steering Committee members and those providing participant care, monitoring or managing data, or adjudicating endpoints were blinded. For participant safety, an independent Data and Safety Monitoring Board was not blinded. In addition, two programmers and the study statistician who performed analyses for the safety monitoring board had access to either the allocation schedule or to the unblinded lipid value.

Baseline measurements on the day of randomization included lipid analysis (including Apo A1 and Apo B), hematology, blood chemistry and urinalysis.

During the first 48 weeks of active treatment, participants returned to clinic at 6 week intervals. At each visit, participants were asked about adverse events and underwent laboratory safety tests for liver enzymes and creatine kinase. Every 12 weeks, participants also receive dietary reinforcement. During the first 6 months, a lipid profile was performed at every visit. At Week 48, participants received dietary advice and underwent an extensive evaluation that included the tests routinely done at each visit, as well as physical exam, electrocardiogram, mammography (women), ophthalmological examination (San Antonio clinic only), complete blood chemistry, hematology and urinalysis.

After Week 48, the interval between visits was longer (Week 60, Month 18, then every 6 months). At week 60 and at all "mid-year" visits, adverse experience inquiry and laboratory safety tests were performed. The year-end visit included all tests and observations described at the Week 48 visit. At Week 48 and Year 5, Apo A1 and Apo B were measured. At all protocol visits, pharmacists assessed compliance by pill counts.

To attempt to achieve an on-treatment LDL-cholesterol of 110 mg/dl or lower, participants in the lovastatin treatment group could be titrated to lovastatin 40 mg once a day based upon LDL-cholesterol values at 6 and 12 weeks after randomization. Participants in the lovastatin treatment group with LDL-cholesterol >110 mg/dl at both visits were titrated at week 18 to 40 mg once a day of lovastatin by taking two 20 mg tablets once a day. To maintain the blind, an equal number of randomly selected participants in the placebo treatment group were also titrated to two tablets per day. To maintain the blind, an equal number from the titrated placebo group also had their doses reduced. Participants were flagged for withdrawal by the unblinded programmer, if LDL-cholesterol values >195 mg/dl on successive visits following titration. The investigator, the participant and those involved in the participant's care were not unblinded to treatment group or during double blind.

The primary endpoint events included sudden cardiac death, fatal and non-fatal myocardial infarction and unstable angina. They are defined as follows:

I. Fatal Myocardial Infarction or Sudden Cardiac Death

The definition requires that there be no non-cardiac cause of death and one of the following:

Fatal Myocardial Infarction—death within 28 days from the onset of symptoms of a definite acute myocardial infarction Witnessed Unexpected Sudden Cardiac Death—within 1 hour of symptoms Death occurring >1 hour but <24 hours after collapse Unwitnessed Unexpected Death, Presumed Sudden—must have confirming autopsy data or, if autopsy not performed, preceding history of CHD events or symptoms II. Non-Fatal Myocardial Infarction Acute Q-Wave Myocardial Infarction—requires definitive ECG Acute Non-Q-Wave Myocardial Infarction—definitive ECG or, if equivocal, enzymes must be diagnostic. Non-Q-Wave Myocardial Infarction includes myocardial infarctions reperfused by either mechanical or pharmacologic means providing there is supporting ECGs and enzyme data Silent Subclinical (Remote) Myocardial Infarction—definitive ECG, or, if ECG is equivocal, focal wall motion abnormality consistent with myocardial infarction on rest echo or stress thallium (fixed defect) and on catheterization, a ≧50% stenosis in a major corresponding epicardial vessel. Participants who have had a cardiac catheterization as the first diagnostic test for presumed silent (or remote) myocardial infarction are considered to have met criteria for an endpoint event if the catheterization findings indicate focal wall abnormalities consistent with myocardial infarction and 50% stenosis in a corresponding artery III. Unstable Angina New onset exertional and/or accelerated or rest angina and requires at least one of the following:

Stress perfusion study: 1 mm ST segment changes and reversible defect

90% epicardial vessel stenosis or 50% stenosis in the Left Main

≧1 mm ST segment changes with pain on stress testing and/or resting ECG and evidence of 50% stenosis in a major epicardial vessel Note that 'angina' was adjudicated as a secondary endpoint event if, prior to the hospitalization, the participant was asymptomatic for >2 weeks or has been stable for >1 month (defined as 28 days) even if the criteria for 'unstable angina', noted above, were met.

All subjects were followed until the decision to end the study after a median duration of 5.2 years of treatment.

The trial design for the final analysis provided 90 to 97% power, respectively, to detect the reductions in the number of patients experiencing as a first event any of those shown in the following Table 1:

TABLE 1

EFFICACY ENDPOINTS

| ENDPOINTS | Risk Reduction | Relative Risk (C.I.) |
| --- | --- | --- |
| Primary Endpoint: acute major coronary events defined as fatal and non-fatal myocardial infarction, unstable angina or sudden cardiac death | 37% | 0.63 (0.50, 0.79), p = 0.00008 |
| Secondary Endpoints | | |
| Revascularizations | 33% | 0.67 (0.52, 0.85), p = 0.001 |
| Unstable Angina | 32% | 0.68 (0.48, 0.95), p = 0.023 |
| Fatal and Nonfatal MI | 40% | 0.60 (0.43, 0.83), p = 0.002 |
| Fatal and Nonfatal Cardiovascular Events | 25% | 0.75 (0.62, 0.91), p = 0.003 |
| Fatal and Nonfatal Coronary Events | 25% | 0.75 (0.61, 0.92), p = 0.006 |

Thus, the risk of an acute major coronary event using lovastatin was reduced by at least about 20% and more particularly about 21% to 50%, and illustratively about 30% to 40%. The risk reduction of an acute major coronary event with simvastatin, pravastatin, fluvastatin, cerivastatin, or atorvastatin is also expected to be at least about 20%, and more particularly about 21% to 50%, and illustratively about 30% to 40%.

Similarly, the risk of a fatal and non-fatal cardiovascular event using lovastatin was reduced by at least about 9% and more particularly about 9% to 38%, and illustratively about 20% to 30%. The risk reduction of a fatal or non-fatal cardiovascular event with simvastatin, pravastatin, fluvastatin, cerivastatin or atorvastatin is also expected to be at least about 9%, and more particularly about 9% to 38%, and illustratively about 20% to 30%.

Also, the risk of unstable angina using lovastatin was reduced by at least about 5% and more particularly about 5% to 52%, and illustratively about 25% to 40%. The risk reduction of unstable angina with simvastatin, pravastatin, fluvastatin, cerivastatin, or atorvastatin is also expected to be at least about 5%, and more particularly about 5% to 52%, and illustratively about 25% to 40%.

Also, the risk of revascularization using lovastatin was reduced by at least about 15% and more particularly about 15% to 48%, and illustratively about 30% to 40%. The risk reduction of revascularization with simvastatin, pravastatin, fluvastatin, cerivastatin, or atorvastatin is also expected to be at least about 15%, and more particularly about 15% to 48%, and illustratively about 30% to 40%.

Similarly, the risk of a fatal or non-fatal myocardial infarction using lovastatin was reduced by at least about 17% and more particularly about 17–57%, and illustratively, about 30–50%. The risk reduction of a fatal or non-fatal myocardial infarction using simvastatin, pravastatin, fluvastatin, cerivastatin or atorvastatin is also expected to be at least about 17%, and more particularly about 17–57%, and illustratively, about 30–50%.

To further evaluate the effect of treatment, risk reduction for first acute major coronary events (the primary endpoint) was investigated by LDL-cholesterol (LDL-C) and HDL-cholesterol (HDL-C) tertiles at the time of randomization. The results are shown in the following Table 2 (with 95% confidence interval, or 95% C.I.), where "% change" indicates the change in LDL-C or HDL-C, as appropriate, from baseline to the one year point:

TABLE 2

| | % change | Risk Reduction | Relative Risk (95% C.I.) |
|---|---|---|---|
| LDL-C (mg/dl) | | | |
| <142 | −20.1 | 34% | 0.66 (0.43, 1.00) |
| 142.0–156.8 | −26.0 | 36% | 0.64 (0.42, 0.99) |
| >156.9 | −28.9 | 41% | 0.59 (0.41, 0.85) |
| HDL-C (mg/dl) | | | |
| <34.0 | 7.4 | 45% | 0.55 (0.38, 0.82) |
| 34.5–39.5 | 6.2 | 43% | 0.57 (0.39, 0.84) |
| >39.5 | 4.3 | 15% | 0.85 (0.54, 1.32) |

The risk reduction achieved with lovastatin was independent of baseline LDL-C and HDL-C, thus demonstrating that benefit is conferred even in those subjects in the lowest LDL-C tertile. Similar results are also expected to be achieved with simvastatin, pravastatin, fluvastatin, cerivastatin and atorvastatin.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method for preventing or reducing the risk of a first occurrence of a cardiovascular event comprising administering a prophylactically effective amount of an HMG-CoA reductase inhibitor alone or in combination with another lipid altering agent to a subject having a serum high density lipoprotein cholesterol level less than or equal to 50 mg/dl and no history of clinically evident coronary heart disease prior to the initial administration.

2. The method of claim 1 wherein the subject has an average to mildly elevated level of serum low-density lipoprotein cholesterol.

3. The method of claim 2 wherein the subject has a low-density lipoprotein cholesterol level less than or equal to 190 mg/dl.

4. The method of claim 1 wherein the subject has an average to mildly elevated level of serum total cholesterol.

5. The method of claim 1 wherein the subject has a serum triglycerides level of less than or equal to 400 mg/dl.

6. The method of claim 1 wherein the subject has a ratio of total cholesterol/HDL-cholesterol of greater than or equal to 4.5.

7. The method of claim 1 wherein the subject has an to mildly elevated average level of serum low-density lipoprotein cholesterol and an average to mildly elevated level of serum total cholesterol.

8. The method of claim 7 wherein the subject has a ratio of total cholesterol/HDL-cholesterol of greater than or equal to 4.5.

9. The method of claim 8 wherein the subject has a serum triglycerides level of less than or equal to 400 mg/dl.

10. The method of claim 1 wherein the prophylactically effective amount of the HMG-CoA reductase inhibitor is an amount sufficient to lower the subject's low-density lipoprotein cholesterol level to 130 mg/dl or less.

11. The method of claim 10 wherein the prophylactically effective amount of the HMG-CoA reductase inhibitor is an amount sufficient to lower the treated subject's low-density lipoprotein cholesterol level to 115 mg/dl or less.

12. The method of claim 11 wherein the prophylactically effective amount of the HMG-CoA reductase inhibitor is an amount sufficient to lower the treated subjectt's low-density lipoprotein cholesterol level to 110 mg/dl or less.

13. The method of claim 1 wherein the subject has a serum total cholesterol level less than or equal to 260 mg/dl.

14. The method of claim 1 wherein the subject is female and at least 55 years old and has a serum high-density lipoprotein cholesterol level less than or equal to 47 mg/dl.

15. The method of claim 1 wherein the subject is male and at least 45 years old and has a serum high-density lipoprotein cholesterol level less than or equal to 45 mg/dl.

16. The method of claim 1 wherein the reduction of risk of a first occurrence of a cardiovascular event is at least about 10%.

17. The method of claim 16 wherein the reduction of risk of a first occurrence of a cardiovascular event is at least about 20–30%.

18. The method of claim 1 wherein the subject is administered a prophylactically effective amount of an HMG-CoA reductase inhibitor regularly for at least 1 year.

19. The method of claim 18 wherein the subject is administered a prophylactically effective amount of an HMG-CoA reductase inhibitor regularly for at least 2 years.

20. The method of claim 19 wherein the subject is administered a prophylactically effective amount of an HMG-CoA reductase inhibitor regularly for at least 4.5 years.

21. The method of claim 1 wherein the cardiovascular event is selected from the group consisting of fatal and non-fatal acute major coronary events, coronary revascularization procedures, peripheral vascular disease, stable angina, and cerebrovascular accidents.

22. The method of claim 21 wherein the cardiovascular event is selected from the group consisting of fatal and non-fatal acute major coronary events and coronary revascularization procedures.

23. The method of claim 22 wherein the fatal and non-fatal acute major coronary events are selected from the group consisting of fatal myocardial infarction; witnessed and unwitnessed sudden cardiac death and sudden death occurring from 1 hour up to 24 hours after collapse; non-fatal myocardial infarction; definite acute Q-wave myocardial infarction; non-Q-wave myocardial infarction; silent subclinical (remote) myocardial infarction; and unstable angina pectoris.

24. The method of claim 1 wherein the HMG-CoA reductase inhibitor is selected from the group consisting of lovastatin, simvastatin, pravastatin, fluvastatin, atorvastatin, cerivastatin and the pharmaceutically acceptable salt, ester and lactone forms thereof.

25. The method of claim 24 wherein the HMG-CoA reductase inhibitor is selected from the group consisting of lovastatin and simvastatin.

26. A method for preventing or reducing the risk of a first occurrence of a cardiovascular event by at least 20–30% comprising administering a prophylactically effective amount of an HMG-CoA reductase inhibitor to a subject having, prior to the initial administration, a serum high-density lipoprotein cholesterol level less than or equal to 50 mg/dl, a serum low-density lipoprotein cholesterol level less than or equal to 190 mg/dl, a serum total cholesterol level less than or equal to 260 mg/dl, a ratio of total cholesterol/HDL-cholesterol of greater than or equal to 4.5, and no history of clinically evident coronary heart disease.

27. The method of claim 26 wherein the prophylactically effective amount of the HMG-CoA reductase inhibitor is an amount sufficient to lower the subject's low-density lipoprotein cholesterol level to 130 mg/dl or less.

28. The method of claim 27 wherein the prophylactically effective amount of the HMG-CoA reductase inhibitor is an amount sufficient to lower the subject's low-density lipoprotein cholesterol level to 115 mg/dl or less.

29. The method of claim 28 wherein the prophylactically effective amount of the HMG-CoA reductase inhibitor is an amount sufficient to lower the subject's low-density lipoprotein cholesterol level to 110 mg/dl or less.

30. The method of claim 26 wherein the cardiovascular event is selected from the group consisting of fatal and non-fatal acute major coronary events, coronary revascularization procedures, peripheral vascular disease, stable angina, and cerebrovascular accidents.

31. The method of claim 30 wherein the cardiovascular event is selected from the group consisting of fatal and non-fatal acute major coronary events and coronary revascularization procedures.

32. A method of reducing the risk of an acute major coronary event or a coronary revascularization procedure in a human subject with average to mildly elevated LDL cholesterol, below average HDL cholesterol and no symptomatic cardiovascular disease which comprises the administration of a prophylactically effective amount of an HMG-CoA reductase inhibitor.

33. The method of claim 32 wherein the acute coronary event is selected from myocardial infarction, unstable angina and sudden cardiac death.

34. The method of claim 33 wherein the HMG-CoA reductase inhibitor is selected from lovastatin, simvastatin, fluvastatin, cerivastatin and atorvastatin.

35. The method of claim 34 wherein the HMG-CoA reductase inhibitor is lovastatin or simvastatin.

36. The method of claim 32 where the acute coronary event is selected from myocardial infarction and unstable angina.

37. The method of claim 32 wherein the HMG-CoA reductase inhibitor is selected from lovastatin, simvastatin, fluvastatin, cerivastatin and atorvastatin.

38. The method of claim 37 wherein the HMG-CoA reductase inhibitor is lovastatin or simvastatin.

* * * * *

Disclaimer

6,180,660—Edwin J. Whitney, San Antonio, TX; Geraldine Mantell, North Wales, PA. CHOLESTEROL-LOWERING THERAPY. Patent dated January 30, 2001. Disclaimer filed by the assignee December 13, 2004, Merck & Co., Inc.

Hereby disclaim the following complete claims in the above identified patent (1-38).

*(Official Gazette, July 26, 2005)*